United States Patent [19]

Cabri et al.

[11] Patent Number: 5,218,130
[45] Date of Patent: Jun. 8, 1993

[54] 4-SUBSTITUTED ANTHRACYCLINONES AND THEIR PREPARATION

[75] Inventors: Walter Cabri; Silvia De Bernardinis, both of Milan; Franco Francalanci, Novara; Sergio Penco, Milan, all of Italy

[73] Assignee: Farmitalia Carlo Erba S r l, Milan, Italy

[21] Appl. No.: 646,594
[22] PCT Filed: Jul. 24, 1989
[86] PCT No.: PCT/EP89/00869
  § 371 Date: Jan. 25, 1991
  § 102(e) Date: Jan. 25, 1991
[87] PCT Pub. No.: WO90/01490
  PCT Pub. Date: Feb. 22, 1990

[30] Foreign Application Priority Data

Jul. 29, 1988 [GB] United Kingdom ............... 8818167

[51] Int. Cl.$^5$ .................................. C07C 50/00
[52] U.S. Cl. ............................ 552/201; 536/6.4; 552/202; 552/206; 552/207
[58] Field of Search ............... 514/34; 536/6.4; 552/201, 206, 207, 202

[56] References Cited

U.S. PATENT DOCUMENTS

| | | | |
|---|---|---|---|
| 4,046,878 | 9/1977 | Patelli et al. | 514/34 |
| 4,749,693 | 6/1988 | Angelucci et al. | 514/34 |
| 4,891,360 | 1/1990 | Angelucci et al. | 514/34 |
| 4,985,548 | 1/1991 | Caruso et al. | 536/6.4 |
| 4,987,126 | 1/1991 | Bargiotti et al. | 514/34 |
| 5,045,534 | 9/1991 | Bargiotti et al. | 514/34 |

OTHER PUBLICATIONS

J. Chem. Soc., Chem. Commun., 1987, R. E. Dolle et al.: "Palladium catalysed alkoxycarbonylation of phenols to benzoate esters", pp. 904–905.

Die Pharmazie, May 1987, ISSN 0031-7144 Heft 5, Jahrgan 42, pp. 289–303, "Strukturen Der Anthracyclin-Tumoristatica", D. G. Strauss.

The Journal of Antibiotics, Dec. 1981, pp. 1596–1607, "Structure-Activity Relationships of Anthracyclines Relative to Cytotoxicity and Effects on Macromolecular synthesis in L1210 Leukemia Cells", Yasue Matsuzawa, et al.

Chemistry and Industry, Nov. 5, 1984, pp. 766–770, "Anticancer Drugs: DNA—intercalation and free radical attack", Kenneth T. Douglas.

Primary Examiner—Johnnie R. Brown
Assistant Examiner—Elli Peselev
Attorney, Agent, or Firm—Oblon, Spivak, McClelland, Maier & Neustadt

[57] ABSTRACT 4-substituted anthracyclinones of formula (I)

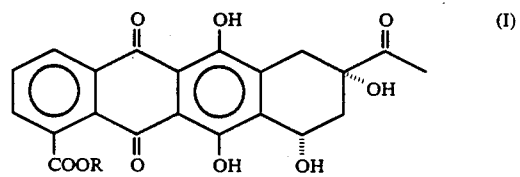

wherein R represents a hydrogen atom or a straight or branched alkyl, alkenyl or alkynyl group having from 1 to 10 carbon atoms, are intermediates in the preparation of antitumor anthracycline glycosides of formula (IX):

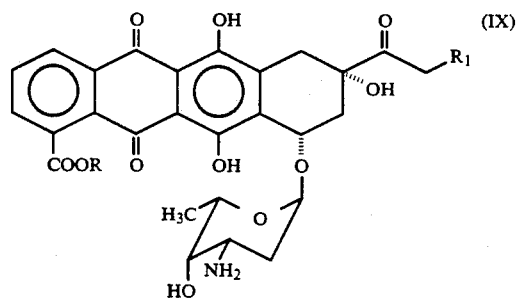

wherein R is as defined above and $R_1$ is a hydrogen atom or a hydroxy group, and pharmaceutically acceptable salts thereof.

7 Claims, No Drawings

4-SUBSTITUTED ANTHRACYCLINONES AND THEIR PREPARATION

The present invention relates to anthracyclinone intermediates and to anthracycline glycosides obtainable therefrom.

According to the present invention, there are provided 4-substituted anthracyclinones of formula (I):

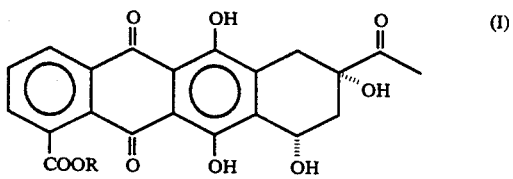
(I)

wherein R represents a hydrogen atom or a straight or branched alkyl, alkenyl or alkynyl group of up to 10 carbon atoms, preferably of up to 4 carbon atoms. Preferred compounds are:
4-demethoxy-4-methoxycarbonyl-daunomycinone and
4-demethoxy-4-(but-3'-en-1'-oxy)carbonyl-daunomycinone.

Compounds of formula (I) are key intermediates for the preparation of antitumor glycosides. Accordingly, the present invention further provides anthracycline glycosides having the formula (IX):

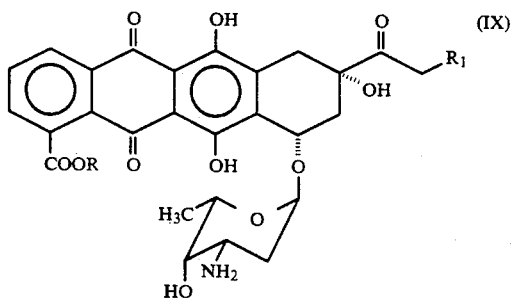
(IX)

wherein R is as defined above and $R_1$ is a hydrogen atom or a hydroxy group; and their pharmaceutically acceptable salts. Preferred acid addition salts are the hydrochloride salts. Preferred compounds are:
4-demethoxy-4-methoxycarbonyl-daunomycin and its hydrochloride.

The present invention also provides a process for the preparation of a 4-substituted anthracyclinone of formula (I) above, which process comprises carbonylating 4-demethyl-4-sulfonyl-13-dioxolanyl daunomycinone of formula (II):

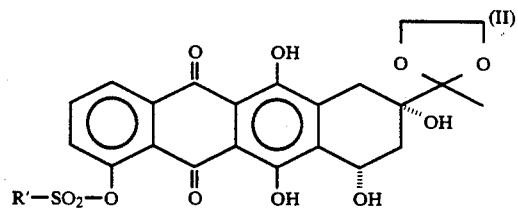
(II)

wherein R' represents an alkyl group of from 1 to 10 carbon atoms optionally substituted by one or more halogen atoms or an aryl group optionally substituted by halogen, alkyl, alkoxy or nitro, with carbon monoxide in the presence of a nucleophile R-OH wherein R is as defined above, an organic or inorganic base and as catalyst a compound of formula (III):

$ML_nL'_m$ (III)

wherein M represents a transition metal atom, L and L', which are the same or different, each represent an anion or a neutral molecule and n and m may vary from 0 to 4, to obtain a compound of formula (V):

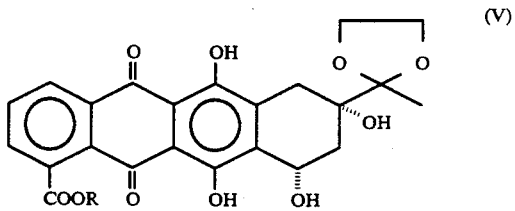
(V)

wherein R is as defined above; and removing the 13-oxo protecting group by acid hydrolysis.

The invention additionally provides a process for the preparation of an anthracycline glycoside of formula (IX) or a pharmaceutically acceptable salt thereof, which process comprises:

(i) reacting a 4-substituted anthracyclinone of formula (I) with a halosugar of formula (X):

(X)

wherein Hal represents a halogen atom, the 3"-amino group is protected or unprotected and the 4"-hydroxy group is protected or unprotected; and, if present, removing the or each protecting group from the product thus-obtained such as to obtain an anthracycline glycoside of formula (IX) wherein $R_1$ is a hydrogen atom;

(ii) if desired, converting the said glycoside of formula (IX) thus obtained into a pharmaceutically acceptable salt thereof;

(iii) if desired, brominating the said glycoside of formula (II) or pharmaceutically acceptable salt thereof and hydrolysing the 14-bromo derivative thus obtained so as to form the corresponding glycoside of formula (IX) wherein $R_1$ is a hydroxy group; and (iv) if desired, converting the said glycoside of formula (IX) wherein $R_1$ is hydroxy into a pharmaceutically acceptable salt thereof.

Compounds of formula (I) are obtained from 4-sulfonylanthracyclinones of formula (II)

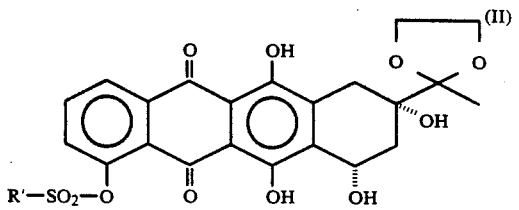
(II)

wherein R' represents an alkyl group having from 1 to 10 carbon atoms; a halo or polyhalo such alkyl group, for example a perfluoroalkyl group; or an aryl group such as a phenyl group optionally substituted by at least one, for example from one to three, halogen atom(s) or alkyl, alkoxy or nitro group(s). The halogen atom may be chloro or fluoro. The alkyl and alkoxy groups may contain from 1 to 10, for example from 1 to 4, carbon atoms. Preferred groups which R' may represent are trifluoromethansulfonyl, 4-fluorophenyl and 4-tolyl.

Compounds of formula (II) can be prepared from naturally occurring daunomycinone (IV) as described in European Applications Nos. 89301282.3 and 89303418.1.

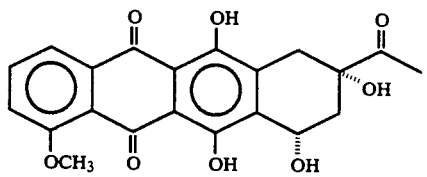

More specifically, a compound of formula (II) can be prepared from (+) daunomycinone of formula (IV) (Scheme 1 below). This can be prepared by a suitable hydrolysis of daunorubicin, in its turn obtained by fermentation as described in U.S. Pat. No. 4,012,284. The daunomycinone is demethylated by treatment with $AlCl_3$ in an inert organic solvent such as nitrobenzene at the reflux temperature to give 4-demethyldaunomycinone, which is called also carminomycinone (VI). Such a process is described in U.S. Pat. No. 4,188,377.

The 13-keto group of 4-demethyldaunomycinone is protected by treatment with ethylene glycol in the presence of p-toluenesulfonic acid at the reflux temperature. The resultant compound of formula (VII) is sulfonated at position C4-OH to give a compound of formula (II), without any protection of the remaining OH groups. The sulfonating agent is a sulfonyl chloride of formula (VIII):

 R'-SO$_2$Cl (VIII)

wherein R' is as defined above. Preferably the reaction is carried out in pyridine. It should be stressed that this selective sulfonylation does not affect either the phenolic C6-OH and C11-OH or the benzylic C7-OH only under specific conditions, namely reacting the 4-demethyldaunomycinone derivative (VI) with the sulfonyl chloride in the presence of N,N-diisopropylethylamine and a catalytic amount of 4-dimethylamino pyridine.

The process of the invention allows the formation of a carbon-carbon bond at position C-4 under mild conditions to give compounds of formula (I) which would otherwise be accessible only by total chemical synthesis. Moreover it is noteworthy that none of the remaining functional groups is affected by the reaction and the stereochemistry at C-7 and C-9 is completely preserved.

More particularly compounds of formula (I) are prepared by reacting compounds of formula (II) with carbon monoxide in a solvent containing a suitable nucleophile ROH, wherein R is as defined above, in the presence of a compound of formula (III) (hereunder referred to as catalyst):

 ML$_n$L'$_m$ (III)

wherein M represents a transition metal atom, L and L', which may be the same or different, may be an anion such as Cl$^-$ or CH$_3$COO$^-$ or a neutral molecule such as a solvent molecule, a mono- or di-phosphine, a phosphite or a diamine; n and m may vary from 0 to 4. Typically m+n is at least 1, for example 1, 2, 3 or 4. Preferred transition metal atoms which M may represent are palladium or nickel. Preferred groups which L and/or L' may represent are chelating diphosphines such as 1,3-diphenylphosphinopropane or 1,1'-bis-(diphenylphosphino)ferrocene. The compound of formula (II) is therefore carbonylated with a transition metal complex, preferably one between a transition metal atom such as palladium or nickel and a chelating ligand as above. The molar ration of transition metal atom:chelating ligand is from 1:1 to 1:4.

Compounds of formula (II) are typically dissolved in an appropriate polar solvent and added, under a carbon monoxide atmosphere, to a solution of catalyst, either preformed or generated "in situ" from suitable precursors in the presence of a nucleophile ROH and a base. Suitable bases are trialkylamines and alkali or alkaline earth metal carbonates or hydroxides. The temperature of the reaction is typically from 0° to 150° C., preferably between 30° and 100° C., and the catalyst is generally used in a molar ratio to (II) from 1:1 to 1:10000, preferably between 1:20 and 1:1000. The CO pressure may vary from 101 to 101×10$^2$ kPa (1 to 100 atm.), preferably from 101 to 101×10 kPa (1 and 10 atm.).

Compounds thus obtained of general formula (V):

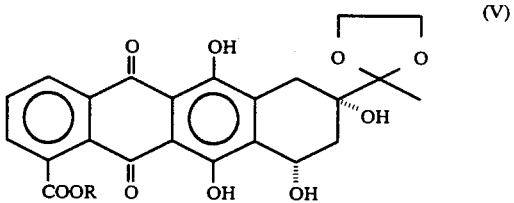

wherein R is as defined above, are easily transformed into the final products (I) by acid hydrolysis of the protecting group at the C-13 carbonyl. The compounds (I) are recovered.

In a preferred embodiment, the 4-demethyl-4-sulfonyl-13-dioxolanyl daunomycinone of formula (II), dissolved in dioxane or dimethylformamide, is reacted at from 0° to 150° C. in the presence of the nucleophile R—OH wherein R is as defined above the organic or inorganic base and the catalyst of formula (III) in which M represents palladium or nickel, L and L' each independently represent Cl$^-$, CH$_3$COO$^-$, a solvent molecule, a mono- or di-phosphine, a phosphite or a diamine and m+n is 1, 2, 3 or 4, to obtain the compound of formula (V) which, after treatment at 0° C. and for 15 minutes with trifluoroacetic acid, gives the 4-alkoxycarbonyl anthracyclinone of formula (I) which is subsequently purified by chromatography on a silica gel column using as eluent system chloroform-acetone (95:5 v/v).

SCHEME 1

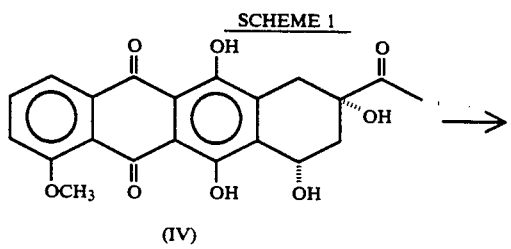

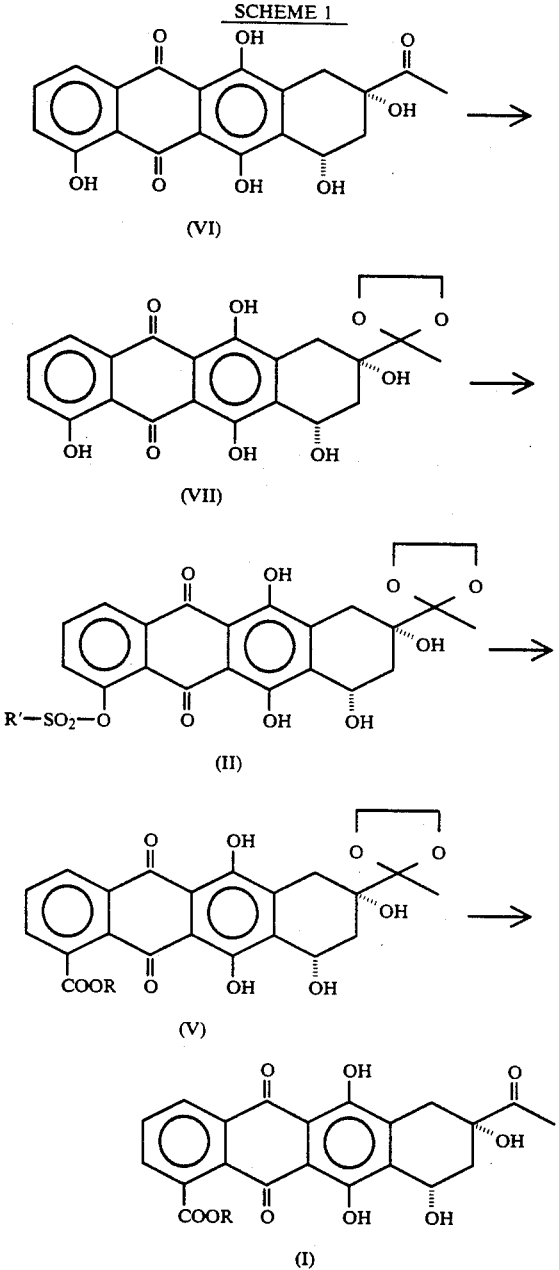

The carbonylation of aryl sulfonates has already been described for simple molecules (Tetrahedron Lett. 27 (1986) 3931; J. Chem. Soc. Chem. Comm. (1987) 904; J. Am. Chem. Soc. 110 (1988) 1557) but it has never been reported in anthracycline chemistry, probably because of the presence of other interferring functional groups. The problems arising from the presence of said groups, namely aromatization of ring A, formation of 7-deoxy derivatives, hydrolysis of the 4-sulfonyl derivative and-/or modifications of the quinone moiety can be suppressed under the conditions of the invention. Moreover, ester compounds of formula (I) can be easily transformed into other derivatives by conventional techniques; e.g. the corresponding amides may be prepared by treatment with a suitable amine.

An anthracycline glycoside of formula (IX) in which $R_1$ is a hydrogen atom is prepared by reacting an anthracyclinone of formula (I) with a halosugar of formula (X). In formula (X), Hal is typically a chlorine atom. If the 3''-amino group is protected, the protecting group may be a trifluoroacetyl group. If the 4''-hydroxy group is protected, the protecting group may also be a trifluoroacetyl group. The condensation of the anthracyclinone of formula (I) and halosugar of formula (X) generally takes place in the presence of silver trifluoromethanesulfonate (triflate).

The anthracyclinone may be dissolved in an inert organic solvent such as methylene dichloride, with the reaction taking place under an inert atmosphere such as argon at a temperature of from 5° to 30° C., typically at ambient temperature. Any protecting groups may be removed by mild alkaline hydrolysis, for example by treatment with 0.1N aqueous sodium hydroxide. Preferably the anthracycline glycoside is isolated as its hydrochloride by treatment of the free base with methanolic hydrogen chloride.

The anthracycline glycoside of formula (IX) in which $R_1$ is a hydrogen atom, or one of its salts, can be converted into the corresponding doxorubicin derivative in which $R_1$ is a hydroxy group by bromination at the 14-position and by hydrolysis of the 14-bromo derivative with aqueous sodium formate. The bromination and hydrolysis conditions are typically those described in U.S. Pat. No. 4,122,076 or GB-A-1217133.

More specifically, the glycoside of formula (IX) in which $R_1$ is a hydrogen atom, or one of its salts, can be reacted with bromine in chloroform to obtain a 14-bromo derivative from which, after hydrolysis at room temperature and for 48 hours under nitrogen with an aqueous solution of sodium formate, the compound of formula (IX) in which $R_1$ is hydroxy is obtained as a free base and, by treatment with anhydrous methanolic HCl, is isolated as its hydrochloride.

The invention provides pharmaceutical compositions comprising an anthracycline glycoside of formula (IX) or a pharmaceutically acceptable salt thereof, together with a pharmaceutically acceptable diluent or carrier. Conventional carriers and diluents may be used. The composition may be formulated and administered in conventional manner.

The compounds of the invention are useful in methods of treatment of the human or animal body by therapy. They are useful as antitumor agents. A therapeutically effective amount is administered to a patient. An amount sufficient to inhibit the growth of the tumour may be administered. The tumor may be a Gross leukaemia tumor.

The following Examples 3 to 8 illustrate the invention.

EXAMPLE 1

4-Demethyl-13-dioxolanyl-daunomycinone (VII)

To a solution of 15.04 g (37.8 mmol) of daunomycinone (IV) in 1.4 l of methylene chloride, under stirring in a nitrogen atmosphere, 52.8 g (396.4 mmol) of anhydrous aluminium chloride were added portionwise over a period of 1.5 hour. The reaction mixture was refluxed for one hour, then the solvent was distilled off. A solution of 22.8 g (25.4 mmol) of oxalic acid in 200 mL of water cooled at 0° C. was carefully added to the residue and the mixture stirred for two hours at room temperature. The solid was recovered by filtration, washed with water and suspended in benzene (400 mL). Ethylene glycol (30 mL) and p.toluene sulfonic acid (0.3 g) were then added and the reaction mixture was refluxed with azeotropic removal of water for ca. 6 hours. After cooling to room temperature the solid was recovered by filtration and washed with water and ethanol to give, after drying, 11.3 g of (VII). The product showed on HPLC analysis to be of 98% purity.

HPLC analysis:
Column: MERCK RP 18/7 μm (250×4.2 mm),

| Mobile phase: | |
|---|---|
| A- 0.01 M Sodium heptansulfonate/0.02 M phosphoric acid | 6 |
| Acetonitrile | 4 |
| B- Methanol | 7 |
| Acetonitrile | 3 |

Gradient: from 20% B to 70% B in 25 min,
Flow rate: 1.5 mL/min,
Detector: UV at 254 nm.

$^1$H-NMR 300 MHz (in CDCl$_3$): δ=1.42 (3H,s), 1.94 (1H,dd), 2.42 (1H,dt), 2.75 (1H,d), 3.18 (1H,dd), 4.04 (4H,s), 5.20 (1h,dd), 7.25 (1H,d), 7.65 (1H,t), 7.84 (1H,d), 12.18 (1H,s), 12.92 (1H,s), 13.52 (1H,s).

M.S.: m/z=428 (M+,base peak).

TLC on Kieselgel plate F 254 (MERCK) using chloroform/acetone (8:2 by volume) Rf=0.52.

EXAMPLE 2

4-Demethyl-4-trifluoromethansulfonyl-13-dioxolanyl daunomycinone (II; R'=CF$_3$)

To a solution in pyridine (1.1 L) of 11 g (25.7 mmol) of (VII), 22 mL (128.5 mmol) of diisopropylethylamine and 3.8 g (25.7 mmol) of 4-dimethylaminopyridine, cooled at 0° C., 12.7 mL (75.5 mmol) of trifluoromethansulfonyl anhydride were added and the reaction mixture was stirred for 1 hour at room temperature. The reaction mixture was then cooled at 0° C. and added with 5 L of methylene chloride and 3 L of 10% hydrochloric acid. After separation the organic phase was washed with water, dried over sodium sulfate and the solvent evaporated under reduced pressure to leave 13.75 g of solid which was refluxed for 15 minutes in ethanol (350 mL) and filtered obtaining 8.25 g of (II; R'=CF$_3$). (HPLC: 91%, conditions as described in example 1).

$^1$H-NMR 300 MHz (in CDCl$_3$): δ=1.47 (3H,s), 1.98 (1H, dd,), 2.45 (1H, d), 2.79 (1H, d), 3.21 (2H, m), 3.82 (1H, bs), 4.09 (4H, s), 5.27 (1H, bs), 7.63 (1H,d), 7.88 (1H, t), 8.48 (1H,d), 13.26 (1H,s), 13.48 (1H,s).

M.S.: m/z=560 (M+, base peak).

TLC on Kieselgel plate F 254 (MERCK) using chloroform/acetone (8:2 by volume) Rf=0.56.

EXAMPLE 3

4-Demethoxy-4-methoxycarbonyldaunomycinone (I; R=CH$_3$)

To a solution of 1 g of 4-demethyl-4-trifluoromethansulfonyl-13-dioxolanyl daunomycinone (II; R'=CF$_3$) (1.78 mmol) in 50 mL of dioxane, under a carbon monoxide atmosphere, were successively added 0.85 mL of tri-n.butylamine, 3 mL of methanol, 37 mg of 1,3 diphenylphosphinopropane (0.089 mmol) and 20 mg of Palladium acetate (0.089 mmol). The reaction mixture was stirred at 60° C. until the CO absorption stopped, then cooled to 0° C., acidified with 10% hydrochloric acid and extracted with methylene chloride. The organic phase was evaporated to dryness leaving 0.82 g of crude 4-demethoxy-4-methoxycarbonyl-13-dioxolanyl daunomycinone (V; R=CH$_3$), (HPLC 95%).

$^1$H-NMR 300 MHz (in CDCl$_3$): δ=1.98 (1H, dd, J=14.5;4.7 Hz), 2.47 (1H, d, J=14.5 Hz), 2.79 (1H, d, J=19 Hz), 3.1–3.32 (2H, m), 3.87 (1H, bs), 4.02 (3H, s), 4.1 (4H, s), 5.26 (1H, bs), 7.72 (1H, dd, J=7.7;1.2 Hz), 7.85 (1H, t, J=7.7), 8.42 (1H, dd, J=7.7;1.2 Hz), 13.18 (1H, s), 13.26 (1H, s).

U.V. (in EtOH): =523, 490, 462, 286, 254, 206 nm; max=254 nm.

I.R. (KBr pellet): =3510, 3390, 1736, 1623, 1575 cm$^{-1}$.

[α]$_D^{20}$ (c=0.1 in dioxane)=+133'

M.S. m/z=470 (M+, base peak)

TLC on Kieselgel plate F 254 (Merck) using chloroform/acetone (9:1 by volume) Rf=0.28

The crude 4-demethoxy-4-methoxycarbonyl-13-dioxolanyl daunomycinone was stirred at 0° C. in 15 ml of trifluoroacetic acid and 0.25 ml of water for 15 minutes. The reaction mixture was diluted with 150 ml of water and extracted with methylene chloride. The organic layer was washed with saturated sodium bicarbonate and water till neutrality, dried over sodium sulfate and evaporated to dryness. The residue was chromatographated on silica gel (chloroform/acetone 95:5 by volume as eluant) obtaining 0.542 g (71.5% from II; R'=CF$_3$) of 4-demethoxy-4-methoxycarbonyl daunomycinone (I; R=CH$_3$),(HPLC 98%).

$^1$H-NMR 300 MHz (in CDCl$_3$):δ=2.04 (1H, dd, J=14.5;4.7 Hz), 2.32 (1H, d, J=14.5 Hz), 2.45 (3H, s), 2.87 (1H, d, J=19 Hz), 3.08 (1H, dd, J=19;1.8 Hz), 4.02 (3H, s), 4.21 (1H, bs), 4.76 (1H, s), 5.21 (1H, bs), 7.71 (1H, dd, J=7.7;1.2 Hz), 7.87 (1H, t, J=7.7 Hz), 8.38 (1H, dd, J=7.7;1.2 Hz), 12.88 (1H, s), 12.98 (1H, s).

U.V. (in EtOH): λ=522, 489, 461, 285, 253, 206 nm; λmax=253 nm.

I.R. (KBr pellet): ν=3440, 1735, 1713, 1622, 1576 cm$^{-1}$.

[α]$_D^{20}$ (c=0.1 in dioxane)=+145'

M.S. m/z 426 (M+, base peak)

TLC on Kieselgel plate F 254 (MERCK) using chloroform/acetone (9:1 by volume) Rf=0.40.

EXAMPLE 4

(I, R=CH$_3$)

The reaction was carried out as described in example 3, except that dimethylformamide (50 mL) was used as solvent and 1,1' bis-(diphenylphosphino) ferrocene (49 mg, 0.089 mmol) as ligand for palladium, obtaining 0.456 g of 4-demethoxy-4-methoxycarbonyl daunomycinone (I, R=CH$_3$),(HPLC 97.6%). Yield from (II) 60%.

EXAMPLE 5

(I, R=CH$_3$)

The reaction was carried out as described in example 3, except that dimethylformamide (50 mL) was used as solvent and 1,2 bis-[N-(1-phenylethyl), N-(diphenylphosphino)amino] ethane (57 mg, 0.089 mmol) was used as ligand for palladium, obtaining 0.500 g of 4-demethoxy-4-methoxycarbonyl daunomycinone (I, R=CH$_3$), (HPLC 98.2%). Yield from (II) 66%.

EXAMPLE 6

(I, R=CH$_2$—CH$_2$—CH=CH$_2$)

To a solution of 1 g of 4-demethyl-4-trifluoromethansulfonyl-13-dioxolanyl daunomycinone (II, R'=CF$_3$) (1.78 mmol) in 50 mL of dioxane, under a carbon monoxide atmosphere, were successively added 0.5 mL of triethylamine, 3 mL of 3-buten-1-ol, 37 mg of 1,3 diphenylphosphinopropane (0.089 mmol) and 20 mg of palladium acetate (0.089 mmol).

The reaction mixture was stirred at 60° C. until the CO adsorption stopped, then cooled to 0° C., acidified with 10% hydrochloric acid and extracted with methylene chloride. The organic phase was evaporated to dryness and the residue chromatographated on silica gel (chloroform/acetone 95:5 by volume as eluant) obtaining 0.568 g (62,3%) of 4-demethoxy-4-(3'-buten-1'-oxy)-carbonyl-13-dioxolanyl daunomycinone, (HPLC 98%)

$^1$H-NMR 300 MHz (in CDCl$_3$): δ1.97 (1H, dd, J=4.9;14.6 Hz), 2.46 (1H, dt, J=14.6;1.8 Hz), 2.55 (2H, q, J=6.8 Hz), 2.78 (1H, d, J=19 Hz), 3.2 (1H, s), 3.24 (1H, dd, J=19;1.8 Hz), 3.86 (1H, bs), 4.1 (4H, s), 4.5 (2H, t, J=6.8 Hz), 5.1 (1H, d, J=10.2), 5.17 (1H, d, J=17.3 Hz), 5.25 (1H, bs), 5.77–5.93 (1H, m), 7.70 (1H, dd, J=7.7; 1.3), 7.85 (1H, t, J=7.7 Hz), 8.42 (1H, dd, J=7.7; 1.3), 13.18 (1H, s), 13.26 (1H, s).

U.V. (in EtOH): λ=523, 489, 462, 288, 254, 205 nm; λ max=254 nm

I.R. (KBr pellet): ν=3440, 1723, 1624, 1576 cm$^{-1}$.

M.S.: m/z=510 (M, base peak)

TLC on Kieselgel plate F 254 (MERCK) using chloroform/acetone (9:1 by volume) Rf=0.45.

The above product (V, R=CH$_2$—CH$_2$—CH=CH$_2$) was treated with trifluoroacetic acid as described in example 3 to give 0.467 g of 4-demethoxy-4-(3'buten-1'-oxy)carbonyl daunomycinone (I, R=CH$_2$—CH$_2$—CH=CH$_2$), (HPLC 96%) (56.1% from III, R'=CF$_3$).

$^1$H-NMR 300 MHz (in CDCl$_3$): δ=2.10 (1H, dd, J=4.8; 14.7), 2.34 1H, dt, J=14.7; 1.8), 2.44 (3H, s), 2.56 (2H, tq, J=6.7; 1.2), 2.91 (1H, d, J=18.8), 3.15 (1H, dd, J=18.8; 1.9), 4.06 (1H, d, J=5.7), 4.42–4.59 (2H, m), 4.68 (1H, s), 5.11 (1H, d, J=10.2), 5.18 (1H, d, J=17.2), 5.23–5.32 (1H, m), 5.77–5.93 (1H, m), 7.72 (1H, dd, J=7.7; 1.2), 7.88 (1H, t, J=7.7), 8.41 (1H, dd, J=7.7; 1.2), 13.03 (1H, s), 13.09 (1H, s).

U.V. (in EtOH): λ=524, 489, 462, 287, 253, 206 nm; λmax=253 nm

I.R. (KBr pellet): ν=3440, 1732, 1715, 1624, 1577 cm$^{-1}$.

M.S.: m/z=466 (M, base peak)

[α]$_D^{20}$ (c=0.1 in dioxane)=+120'

TLC on Kieselgel plate F 254 (MERCK) using chloroform/acetone (9:1 by volume) Rf=0.50.

EXAMPLE 7

Preparation of 4-(methoxycarbonyl)-4-(demethoxy)-daunomycin hydrochloride

To a stirred solution of 4-(methoxycarbonyl)-4-(demethoxy)-daunomycinone (0.549 g, 1.28 mmol) in CH$_2$Cl$_2$(80 ml), at room temperature, under argon, a solution of chlorodaunosammine (0.599 g, 1.67 mmol) in CH$_2$Cl$_2$ (10 ml) and a solution of AgCF$_3$SO$_3$ (0.431 g, 1.67 mmol) in Et$_2$O (14 mol) were simultaneously added, over a ten minute period. After 30 minutes, 0.135 ml of pyridine were added and the reaction mixture was filtered on dicalite. The solution was washed with HCl 1%, then with water and, after drying (Na$_2$SO$_4$) evaporated in vacuo.

The residue was taken up with acetone (10 ml), cooled to 0° C. and treated with NaOH 0.75M (10 ml). After an hour CH$_2$Cl$_2$ and water were added and the pH was adjusted to 4 with HCl 3%. The aqueous phase was separated, treated with NH$_4$OH 1% to pH 8, and extracted with CH$_2$Cl$_2$ (3×100). The collected organic phases were dried over Na$_2$SO$_4$ and evaporated in vacuo. The product was purified by SiO$_2$ column chromatography (CH$_2$Cl$_2$/MeOH/CH$_3$COOH/H$_2$O=180/25/2/3). The collected fractions were diluted with water and the pH adjusted to 8 with NH$_4$OH 1%. The organic phase was separated, dried and evaporated in vacuo to give 0.302 g of free base.

To a solution of the free base in the minimum amount of CHCl$_3$, 0.255 ml of HCl/MeOH 2.1M were added cooling to about 10° C. The precipitate was filtered, washed with ether and dried, obtaining 0.237 g of the title compound. (HPLC=96.95%)

$^1$H-NMR 200 MHz (DMSO-d6): δ (ppm)=1.16 (3H, d; J=6.9 Hz), 1.71 (1H, m), 1.91 (1H, m), 2.12 (2H, m), 2.28 (3H, s), 2.97 (2H, bs), 3.37 (1H, m), 3.57 (1H, bs), 3.93 (3H, s), 4.21 (1H, q; J=6.9 Hz), 4.94 (1H, bs), 5.30 (1H, bs), 5.49 (1H, d; J=6.1 Hz), 5.59 (1H, s), 7.90 (2H, m), 7.93 (1H, bd; J=7.7 Hz), 8.02 (1H, t; J=7.6 Hz), 8.40 (1H, dd; J=7.7 Hz, J=1.3 Hz), 13.1 (2H, bs).

UV (EtOH):=487.6, 252.4, 205.2 nm. max=252.4 nm.

TLC on Kieselgel plate F 254 (MERCK) using CH$_2$Cl$_2$/MeOH/CH$_3$COOH/H$_2$O (8:2:0.7:0.3 by volume) Rf=0.73

EXAMPLE 8

Preparation of 4-(methoxycarbonyl)-4-(demethoxy)-doxorubicin hydrochloride

The title compound can be prepared from 4-(methoxycarbonyl)-4-(demethoxy)-daunomycin hydrochloride according to the procedure described in U.S. Pat. No. 4,122,076. 0.2 g of the 4-(methoxycarbonyl)-4-(demethoxy)-daunomycin hydrochloride is dissolved in a mixture of anhydrous methanol and dioxane. A solution of 1 g of bromine in 10 ml methylene chloride is added, as described in U.S. Pat. No. 4,122,076, to afford the 14-bromo derivative. The 14-bromo derivative is hydrolysed at room temperature and for 48 hours under nitrogen with an aqueous solution of sodium formate. 4-(Methoxycarbonyl)-4-(demethoxy)-doxorubicin is thus obtained which, by treatment with anhydrous methanolic hydrogen chloride, is isolated as its hydrochloride.

We claim:

1. A 4-substituted anthracyclinone of formula (I):

wherein R represents a hydrogen atom or a straight or branched alkyl, alkenyl or alkynyl group, each of which has up to 10 carbon atoms.

2. A compound according to claim 1, wherein R is a hydrogen atom or a straight or branched chain alkyl, alkenyl or alkynyl group each of which has up to 4 carbon atoms.

3. A compound according to claim 1, which is 4-demethoxy-4-methoxycarbonyl-daunomycinone or 4-demethoxy-4-(but-3'-en-1'-oxy)carbonyl-daunomycinone.

4. A process for the preparation of a 4-substituted anthracyclinone of formula (I) according to claim 1, which process comprises carbonylating 4-demethyl-4-sulfonyl-13-dioxolanyl daunomycinone of formula (II):

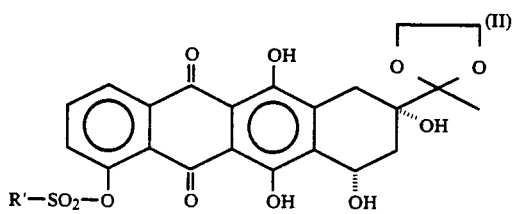

wherein R' represents an alkyl group of from 1 to 10 carbon atoms optionally substituted by one or more halogen atoms or a phenyl group optionally substituted by halogen, alkyl of from 1 to 10 carbon atoms, alkoxy of from 1 to 10 carbon atoms or nitro, with carbon monoxide in the presence of a nucleophile R—OH wherein R is as defined in claim 1, and organic or inorganic base and as catalyst a compound of formula (III):

$$ML_nL'_m \qquad (III)$$

wherein M represents a transition metal atom, L and L', which are the same or different, each represent an anion or a neutral molecule selected from the group consisting of Cl⁻, CH₃COO⁻; mono- or di-phosphine, phosphite and diamine, and n and m are integers from 0 to 4, to obtain a compound of formula (V):

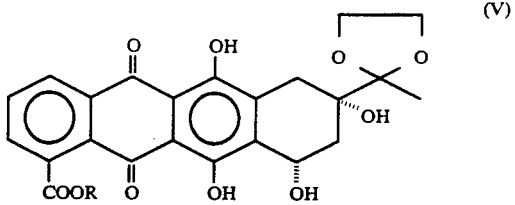

wherein R is as defined above; and removing the 13-oxo protecting group by acid hydrolysis.

5. A process according to claim 4, wherein the 4-demethyl-4-sulfonyl-13-dioxolanyl daunomycinone of formula (II), dissolved in dioxane or dimethylformamide, is reacted at from 0° to 150° C. in the presence of the nucleophile R—OH wherein R is as defined in claim 4, the organic or inorganic base and the catalyst of formula (III) in which M represent palladium or nickel, L and L' each independently represent Cl⁻, CH₃COO⁻, a solvent molecule, a mono- or di-phosphine, a phosphite or a diamine and m+n is 1, 2, 3 or 4, to obtain the compound of formula (V) which, after treatment at 0° C. and for 15 minutes with trifluoroacetic acid, gives the 4-substituted anthracyclinone of formula (I) which is subsequently purified by chromatography on a silica gel column using as eluent system chloroform-acetone (95:5 v/v).

6. A process according to claim 4, wherein the pressure of the carbon monoxide used for the carbonylation is from 101 to 101×10² kPa (1 to 100 atm).

7. A process according to claim 4 wherein the base used in the carbonylation is a trialkylamine or an alkali or alkaline earth metal carbonate or hydroxide and the catalyst, with reference to the starting material of formula (II), is used in a molar ratio from 1:1 to 1:10,000.

* * * * *